(12) United States Patent
Alfaro Santafe et al.

(10) Patent No.: US 9,179,741 B2
(45) Date of Patent: Nov. 10, 2015

(54) METHOD AND DEVICE FOR OBTAINING A PLANTAR IMAGE AND DOUBLE-SIDED MACHINING OF THE INSOLE THUS OBTAINED

(75) Inventors: Victor Alfaro Santafe, Huesca (ES); Javier Alfaro Santafe, Huesca (ES); Carla Lanuza Cerzocimo, Huesca (ES); Angel Perero Lorenz, Huesca (ES); Jose Javier Marin Zurdo, Huesca (ES); Jose Luis Huertas Talon, Huesca (ES); Francisco Valdivia Calvo, Huesca (ES); Juan Jose Aguilar Martin, Huesca (ES); David Guillonia Sanbartolome, Huesca (ES); Carlos Cajal Hernando, Huesca (ES)

(73) Assignee: PODO ACTIVA, S.L., Huesca (ES)

( * ) Notice: Subject to any disclaimer, the term of this patent is extended or adjusted under 35 U.S.C. 154(b) by 1333 days.

(21) Appl. No.: 13/003,856

(22) PCT Filed: Jul. 15, 2009

(86) PCT No.: PCT/ES2009/070290
§ 371 (c)(1),
(2), (4) Date: Mar. 29, 2011

(87) PCT Pub. No.: WO2010/007200
PCT Pub. Date: Jan. 21, 2010

(65) Prior Publication Data
US 2011/0313321 A1    Dec. 22, 2011

(30) Foreign Application Priority Data

Jul. 16, 2008   (ES) .................................. 200802122
Jul. 10, 2009   (ES) .................................. 200930435

(51) Int. Cl.
*A43B 7/14*   (2006.01)
*A43D 39/00*  (2006.01)
(Continued)

(52) U.S. Cl.
CPC ................. *A43D 39/00* (2013.01); *A43D 1/025* (2013.01); *A61B 5/103* (2013.01); *A61B 5/1077* (2013.01); *A61B 5/6829* (2013.01)

(58) Field of Classification Search
CPC ............................... A43D 1/025; A43D 39/00
USPC ............................... 12/146 M, 142 R; 36/145
See application file for complete search history.

(56) References Cited

U.S. PATENT DOCUMENTS 6,205,230 B1    3/2001   Sundman et al.
2001/0030297 A1   10/2001   Milioto et al.
(Continued)

FOREIGN PATENT DOCUMENTS

ES       2101857 A    7/1997
WO    2004071297 A    8/2004

*Primary Examiner* — Brian Szmal
(74) *Attorney, Agent, or Firm* — Lucas & Mercanti, LLP

(57) ABSTRACT

Method for obtaining a plantar image using means for securing and tightening an elastic membrane, as well as to the double-sided machining of the obtained insole, said means taking the form of two adjustable horizontal bars positioned on a scanner or a plurality of cameras and an anti-reflective lens, wherein a membrane is positioned between said horizontal bars and secured using T-flat bars; the stress of the membrane being adjusted using a handle; the foot is positioned on the membrane; an image is taken; and the insole is subjected to double-sided machining on the basis of the image of the surface provided in STL format, with the aid of a securing device that enables the pieces to be rotated up to 180°.

The device used includes a plurality of supporting bars with two adjustable horizontal bars, wherein the elastic membrane is adjusted and tightened using T-flat bars and a handle.

14 Claims, 2 Drawing Sheets

(51) Int. Cl.
*A43D 1/02* (2006.01)
*A61B 5/103* (2006.01)
*A61B 5/107* (2006.01)
*A61B 5/00* (2006.01)

(56) References Cited

U.S. PATENT DOCUMENTS

2006/0283243 A1 12/2006 Peterson et al.
2007/0043582 A1 2/2007 Peveto et al.

METHOD AND DEVICE FOR OBTAINING A PLANTAR IMAGE AND DOUBLE-SIDED MACHINING OF THE INSOLE THUS OBTAINED

DESCRIPTION

The present application is a 371 of International application PCT/ES2009/070290 filed Jul. 15, 2009, which claims priority of ES P200802122, filed Jul. 16, 2008, and ES P200930435, filed Jul. 10, 2009, the contents of all three applications are incorporated herein by reference.

Method and device for obtaining a plantar image using means for securing and tightening an elastic membrane, as well as double-sided machining the insole thus obtained.

OBJECT OF THE INVENTION

The present invention describes the method and device for obtaining a plantar image using means for securing and tightening an elastic membrane, as well as double-sided machining the insole thus obtained. The appropriate tool that allows distributing an even stress across the entire sole of the foot has been developed, which prevents the heel area and the metatarsal area from suffering excessive deformation (flattening) when the sole of the foot is positioned on the glass of a scanner.

BACKGROUND OF THE INVENTION

When the foot is positioned on the glass of a scanner, the heel area and the metatarsal area suffer a deformation (flattening), which causes the scanned image not to be suitable for making an insole or orthoses that can be perfectly adapted to the entire sole of the foot in order to spread the load during walking.

In order to solve this problem a tool that allows distributing an even stress across the entire sole of the foot, similar to walk on the sand, has been designed. For this purpose, an elastic mesh has been suspended on two bars adjustable in height and width, thus by using a handle it is possible to increase or decrease the stress. The system allows varying the rubber stress, as it includes two roulettes allowing through their rotation increasing or decreasing the stress of the membrane and thus adapting it to the patient weight. Furthermore, with the feet image taken by the scanner and the membrane, the automated double-sided machining is achieved based on the image taken, using a turner and the developed software, thereby the insole can be obtained with or without holes for allowing transpiration.

The system is capable of utilizing a plurality of cameras for obtaining images, allowing it to be used for obtaining images from any body part, including full body, in order to develop prostheses.

Currently, and as for systems for obtaining a plantar image, there is no scanner on the market that provides the described possibility therein, using the aforementioned elastic mesh. Double-sided machining insoles do exist, but it is a manual, almost crafted, method.

Vision measurement equipments usually have built therein a camera with a laser generator constituting the triangulation measurement probe itself. The laser generator fits at its end an optic that allows converting the laser spot beam in a range of beams making up a flat geometry, and with a preselected fixed opening angle for covering the object width. The laser light projection from this plane onto the piece or object subjected to be measured generates a light line reflected therefrom, which is taken by the camera, being desirable that only appears the previous light source in the capture site, so as not to obtain spurious points outside the laser plane wherewith the measurement is made. Additionally, in this type of configuration there is a relative movement between the probe and the object to be measured. A synchronized position and image sequence allowing spatially reconstructing all points of the taken lines corresponding to successive cuts of the laser plane is obtained by using the object measured during the movement.

As a prior stage to the measurement, a method for calibrating the camera-laser probe and characterizing the movement axis with respect to thereof has to be performed, using an object pattern with well-known geometry. These systems are called sweep laser triangulation systems and are usually used to digitize the sole of the foot. The fixed and relative arrangement between the camera's optical axis and the laser plane, as well as their relative position with respect to the surface during the sweep, make possible to obtain an increase or decrease of slenderness on the line taken by the camera, leading to a equipment accuracy loss, or a geometric information loss of certain areas due to absence of obtained points. The movement control and its synchrony with the camera have also associated errors.

Furthermore, the incorporation of a single camera in these equipments raises the problem that during the sweep of a free surface with more or less pronounced concavities or convexities, as the sole of a human foot, the line concealment can be produced. To avoid this, a variant consists of arranging the laser perpendicular to the surface of two cameras, such that the line always appears in one of the two images. But these equipments pose a number of problems:

- To integrate a mechanical component subject to wear, inaccuracy sources and reliability problems. The relative accuracy positioners (ball screws or belt transmission with a ruler or linear encoder) significantly increase the equipment price.
- A laser diode is used as a light generator and calibrated measuring element, which raises the problem of its useful life, and the need for performing adjustments and recalibration by qualified personnel at least at the end of its useful life.
- The patient has to keep the foot in the possible most static position during long time for obtaining the image and position sequence. Any slight movement involves direct errors in the geometry that may go unnoticed.
- The aligned arrangement of the cameras and the laser along the longitudinal axis of the foot does not offer an optimal perspective to digitize its side edges up to a certain height, because of its sharp curve in certain areas of the foot sides.

DESCRIPTION OF THE INVENTION

A plantar scanner is a 3D scanner, normally with non-contact laser beam even though the system can be improved, if instead of using a scanner a plurality of cameras and an anti-reflective crystal are used (Example 2), specifically designed for obtaining a polygonal mesh of the plantar surface. When the foot is positioned on the glass of a scanner it suffers a significant deformation (flattening) in the heel area and in the front area (metatarsal area).

In this case, plantar supports or insoles intended to be obtained as a result of the method for scanning the plantar surface, allow contacting the insole with the entire foot surface, maintaining hollow the space between the insole and the ground in the area corresponding to the arch of the foot. The insole material is specific and its thickness is selected based on patient weight and activity so that it maintain enough elasticity for assisting in positioning the foot in the desired position, but which in turn has some degree of flexibility so as the arch of the foot may stretch, as necessary, in order to continue functioning as damping system for the body. Said insole can function as an independent treatment placed in the patient shoe or sport shoes.

Similarly, it also could be built into the shoe sole itself, so as not to steal foot space and keep a hollow space between the arch area of the insole and the ground. In this case, it is not a removable insole, but it would form an active and inseparable part of the shoe itself.

It is important that, so as the insole to be effective as a therapeutic treatment, the insole surface has to accurately correspond with the plantar surface of the subject, with the foot being positioned in the correct position, and also controlling the ankle, knee and hip position. This purpose is achieved with the patient loaded, that is, the person standing and naturally supporting his/her weight on both feet, and the physician adjusting the position of the foot and ankle in order to achieve the desired correction.

This way to proceed, which is certainly the most likely to provide an insole with the desired therapeutic effect, has the drawback that the foot surface is flattened on the crystal under which the scanner is placed, especially the heel area and the metatarsal area. In turn, soft tissues of the arch of the foot are not captured thereby the resulting insole does not capture the foot with total accuracy. The result of the scanning method under these circumstances is a polygonal mesh almost flat with a very poor relief, i.e., it does not reflect the actual arch of the foot of the subject with the foot loaded and particularly in the mentioned arch of the foot, which is precisely where must be the most influence in obtaining the desired correction in the subject's foot.

The invention proposed herein poses a universal solution for positioning on any plantar scanner and consisting of a device for fastening an elastic membrane in order to make the surface of the foot to remain smooth during the scanning method, and leaving the gap necessary for allowing the physician to be able of correctly positioning the subject's foot and ankle, also, once this image has been processed, the automatically double-sided machining of the insole is achieved by using additional securing and positioning devices, which so far is only manually and almost crafted made.

On the one hand, the proposed invention also enables manufacturing plantar orthoses with a much higher degree of functional accuracy than that obtained by the existing methods in the state of the art. It achieves significant improvements in the treatment results of pathologies related to the stress generated in the sole of the foot, such as plantar fasciitis, heel spurs, Achilles tendon and calf muscle overload, etc.

On the other hand, it also uses the principle of stereometry with reticular or structured marks, requiring in the first case the use of specific epipolar geometry techniques. The use of this technique, in the context of the current problem will require the development and implementation of specific and efficient treatment algorithms, enabling improvements in relation to the current state of the art of the technology. Redundancy techniques will be used to improve measurement accuracy.

Another advantage of the invention is that prevents the use of mechanical components for moving diffraction laser-networks and projectors, whereby decreasing the equipment complexity and the error sources during measurement. By becoming the cameras the cheaper component in these equipments and having eliminated the most expensive lighting components, it is possible to increase their number without significantly increasing the final cost, providing redundancies and a higher effective resolution.

Furthermore, the reliability is significantly increased; lowering costs associated with maintenance and manufacturing, and their productivity and profitability are increased. Also, much reduced capture times are achieved, which enables bringing up the matter of providing videometry near real-time, feature not currently offered, and the possibility of being applied to other future measurement needs.

In order to perfectly adapt the elastic membrane to the ideal surface of the subject's foot, it is necessary to have a device for firmly securing the membrane during the scanning method, bearing in mind that it must support the weight of the subject standing up.

The intended device has two horizontal bars fastening the membrane, which are adjustable both in height from the ground and in distance there between. In turn, these can also rotate about themselves for adjusting the membrane stress by using two roulettes. The height adjustment enables that it can be adapted to different scanners, and the variation of the free distance between the bars is necessary for leaving the space suitable for locating the foot there between, while enabling the physician to be able of introducing his/her hand for positioning the foot both above and below the membrane. In addition, it must be capable of being adjusted by said physician according to his/her needs.

Once the height of the horizontal bars and the distance there between have been adjusted at the discretion of the physician, these would be fixed for the subsequent use of the scanner, since these generally do not need to be changed from one person to another except in exceptional cases. However, it is required to have a mechanism for tightening the membrane and adjusting such stress to the characteristics of each subject, weight and anthropometric dimensions of his/her foot. Unlike the previous one, this adjustment has to be an easy and fast operation because the membrane stress must be adjusted in each case.

Natural rubber and silicone as membrane materials have provided satisfactory results, but any material with similar mechanical properties would be useful. In addition to the necessary characteristics of elasticity and resistance, it is important that the membrane material does not have a dark color, since it would be invisible to most scanners. It is therefore recommended light, preferably white, or even translucent colors, which would also enable capturing the natural color of the foot.

From the image obtained after scanning the foot using the elastic membrane, the geometry of the custom insole is obtained. The obtained insole is double-side machined. This type of insole is already on the market, but the used method is a manual, almost crafted one. In this case, with the foot image taken by the scanner and the membrane, using a device for securing and rotating and the developed software, the automated two-sided machining is achieved, based on the taken image, the insole can be obtained with or without holes enabling perspiration.

In the present invention, on the flexible membrane and on the side exposed to view, i.e. through the bottom of the membrane, lines or other geometric elements are permanently included. These lines or other geometric elements are marked as "targets" commonly used in industrial photogrammetry, wherein on the surface to be measured adhesive dots or marks are placed. Said marks can be performed using techniques such as printing (screen printing with flexible and adherent inks, special for rubber or otherwise) or power laser marking techniques, among other known.

In addition, the system is likely to change the device for obtaining a plantar image, i.e. the scanner, only having as components associated with vision, a plurality of cameras, along with their corresponding optics and a low cost conventional commercial lighting, integrated into an envelope or box geometry of which is designed to achieve an adequate control of conditions in the light reaching the membrane enveloping the sole of the patient's foot, and which is returned to the cameras. The arrangement of these lighting elements in the envelope manages to prevent the direct light emission to the object and achieve the formation in the camera(s) of a clear and evenly lit image, with intensity and homogeneous distribution of the "targets" deformed according to the foot geometry, preventing unwanted light reflections and gradients.

Thus, the equipment achieves measuring entire plantar geometries of the foot, adjusting the membrane stress, by using photogrammetry without structured light (geometrically ordered), quickly and in advantageous conditions from the medical point of view, since as mentioned, the geometry of the plant foot is not measured with the foot loaded on a crystal exerting pressure thereon, nor with complete discharge with the foot in the air or without supporting it on any surface, as in the cases of current scanners.

DESCRIPTION OF THE DRAWINGS

For completing the description being made and in order to help to a better understanding of the features of the invention, according to two examples of the embodiment thereof, a set of drawings is attached as an integral part of said description, wherein in an illustrative and not limitative manner, the following has been represented.

DESCRIPTION OF THE PREFERRED EMBODIMENTS

Figure 1:
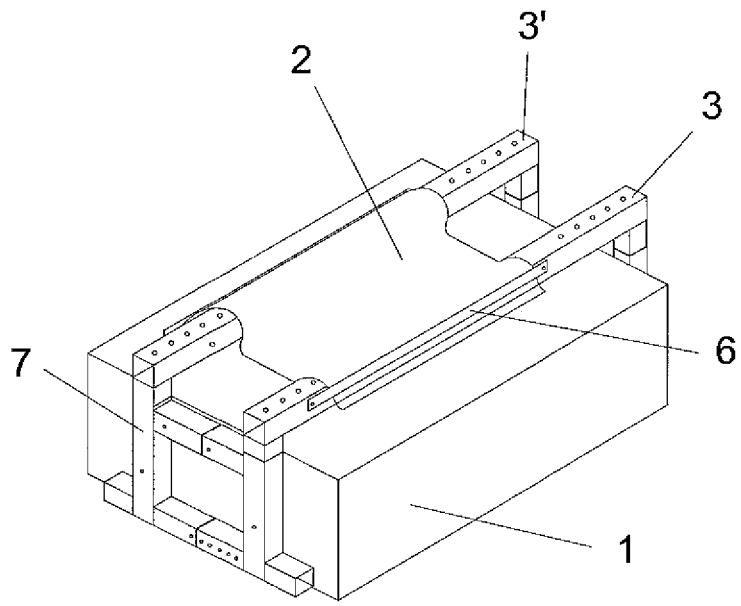
FIG. 1.—shows a perspective view of the device of the invention, without mobile horizontal bars.

In the two following examples two preferred embodiments of the invention are shown, not being one of the examples limited by the other.

EXAMPLE 1

This example consists of a method for obtaining a plantar image using a device with means for securing and tightening an elastic membrane, as well as double-sided machining the obtained insole, comprising the following steps:

(a) positioning the means for securing and tightening, taking the form of two adjustable horizontal bars, on the scanner,
(b) adjusting said horizontal bars both in height and in distance there between,
(c) positioning the membrane on the securing means;
(d) securing the membrane using T-flat bars adhered to the horizontal bars;
(e) adjusting the membrane stress using a handle placed on the side of one of the horizontal bars;
(f) positioning the foot on the membrane and taking the image;
(g) double-sided machining the insole on the basis of the image of the surface provided in STL format with the aid of device for securing and rotating prismatic pieces in machining centres.

For changing the membrane stress is necessary to remove the foot from the device, but the roulettes can be tightened with the patient thereon.

The device used to perform the method for obtaining a plantar image consists of a structure formed by a plurality of support bars (7) on which two horizontal bars (3-3') passing through the scanner (1) from one side to another are placed, these horizontal bars being adjustable both in height and distance there between due to the possibility of extending the support bars (7). An elastic membrane (2) is placed on the horizontal bars (3-3'), adjusted using T-flat bars (6) arranged in the horizontal bars (3-3'), and which is tightened by means of a handle (5).

Figure 2:
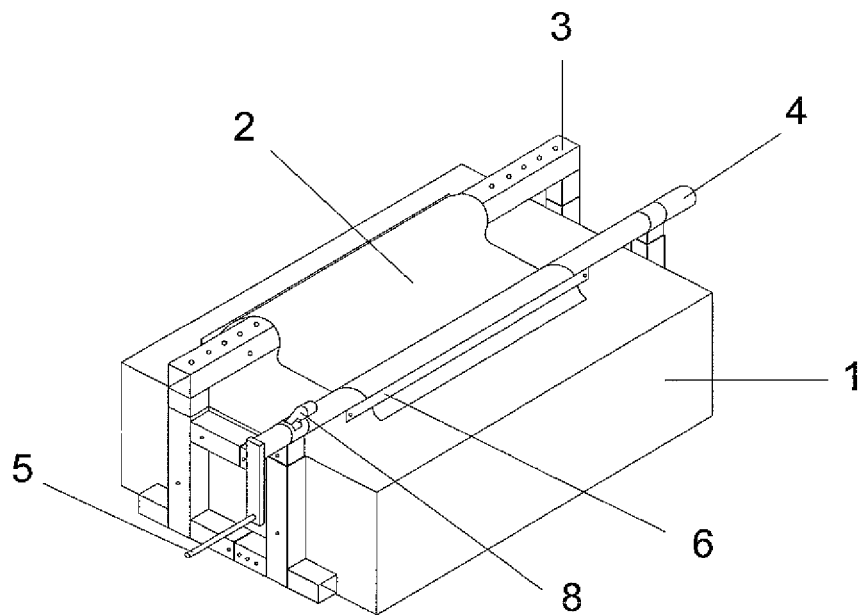
FIG. 2.—shows a perspective picture of the device, wherein one of the horizontal bars is mobile, including a ratchet for preventing unwanted movements.

The horizontal bars (3-3') can be configured so as to rotate, i.e., which in another preferred embodiment, at least one of said horizontal bar is circular, allowing the rotation using a handle (5). These bars are shown in FIG. 2 with the numeral (4).

Thus, in order to avoid unwanted rotations during the scanning method, the horizontal bar (4) has a ratchet mechanism (8) at one of its end.

The membrane (2) used in the method will be made of any material with elasticity and strength characteristics similar to natural rubber and silicone, and of any light color that allows visualizing the foot through the scanner.

Once the plantar image is obtained, the surface model STL is adopted to proceed to machining, using a system for securing and rotating prismatic pieces enabling said pieces to be rotated up to an angle of 180°, and for this purpose the following steps are followed:

obtaining the insole contour; method of great importance because the further development for calculating machining tracks and final cut for removing the insole preform wherein is machined, are based thereon;

obtaining the machining paths;

projecting of the path points on the surface; the obtained points for the 2D path are projected onto the 3D surface for obtaining the coordinates of a point on the surface calculating the end path; the maximum allowable peak height and the diameter of the milling cutter will determine the separation between pitch and pitch and the minimum number of pitches, therefore, the lower the peak, the better the finish, more pitches and more machining time;

drilling breathing holes; in a particular area of the insole (the instep or more away from the ground) an area is marked and certain through holes are drilled therein;

cutting the insole, which is made following the contour using the tool, wherein the tool center is kept at a distance from said contour equal to the radius thereof.

EXAMPLE 2

This example has improved the system for obtaining images, the improvements affect the device for obtaining images, primarily in the scanner (1), so that now the scanner (1) is replaced by a plurality of cameras (10, 11, 12, 13) that obtain the image in real time; the design adds a preferably anti-reflective and safety crystal (14). In general, the method is dynamic, since by tightening the membrane (2) it is observed how the image evolves.

Figure 3:
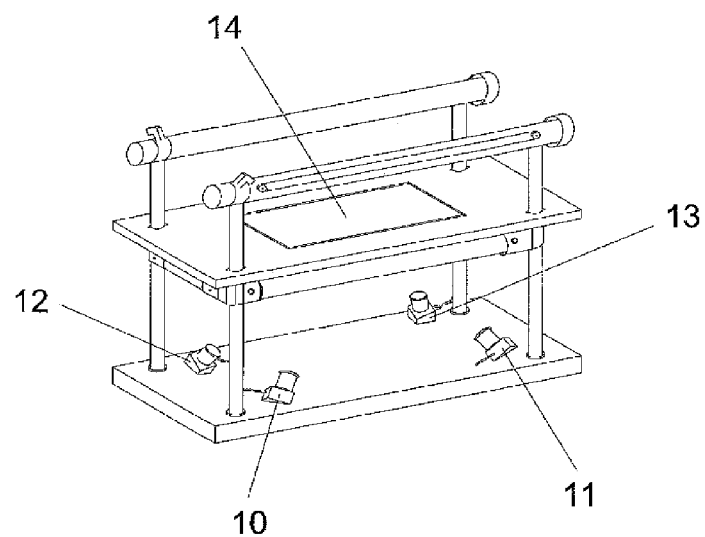
FIG. 3.—shows a view of the device of the invention, wherein instead of having a laser a protector crystal (14) is included, under which a plurality of cameras (10, 11, 12, 13) for taking the image has been placed.

The arrangement of the cameras (10, 11, 12, 13) can open the entire field of measurement, identifying critical imbalances. In this case, in the representation of FIG. 3, four cameras have been preferably arranged, but said number may be variable.

Other improvements proposed for the first example affects the membrane (2). The membrane (2) used in the method will be made of any material with elasticity and strength characteristics similar to natural rubber, silicone, latex or fabrics, it can also be of any color and not necessarily from a clear color. Its elasticity allows it adapting to the geometry to be measured and because of its marks with lines or other type of geometric element, allows the visualization through the cameras (10, 11, 12, 13). The novel feature of this membrane (2) lies in the configuration of the bottom thereof, wherein lines (21) provided with marks or any other type of geometric elements are provided in any orientation, by way of "targets", which may further have a line or several lines (22) with different thicknesses, more or less marked, allowing efficient foot measurement. Areas (23, 23') are those for securing the horizontal bars (3, 4) for tightening and immobilizing the membrane (2).

The orientation of the lines (21) in the membrane plot can be calculated so that the method for identifying the corresponding points within the lines in the taken images reduces to the maximum the multiple intersections of the lines with the epipolar lines. This simplifies the correlation calculation algorithms within the lines before performing the triangulation, but not strictly necessary, since the problem could have also been solved with more complex algorithms slowing down the measurement.

Figure 4:
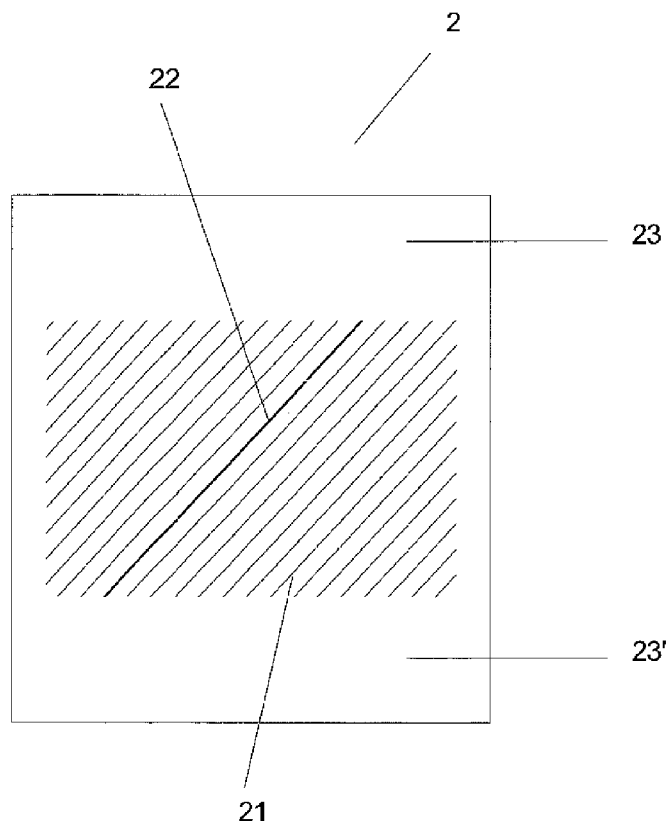
FIG. 4.—shows a view of the bottom of the membrane (2) of the invention, wherein a possible arrangement of lines (21) of the central area, as well as a line (22) thicker than the rest are shown. Areas (23, 23') are those for securing the horizontal bars (3, 4) for tightening and immobilizing the membrane when the image is taken.

As mentioned, optionally any of the lines arranged in the membrane can have greater or smaller thickness for simplifying the correlation calculations between the lines. This is the case of the line (22) observed in FIG. 4.

Importantly, it should be mentioned that this device enables the method to be carried out in a dynamic manner, so that by tightening the membrane (2) how the image evolves, is being seen in real time.

Once the plantar image is obtained, the surface model STL is adopted to proceed to machining, using a system for securing and rotating prismatic pieces enabling said pieces to be rotated up to an angle of 180°, which method is described in Example 1.

The invention claimed is:

1. A method for obtaining a plantar image using a device with means for securing and tightening an elastic membrane, as well as the double-sided machining of the insole thus obtained, wherein the method comprises the following steps:
   (a) positioning the means for securing and tightening, taking the form of two adjustable horizontal bars, on a scanner;
   (b) adjusting said horizontal bars both in height and in distance there between;
   (c) positioning the membrane on the securing means;
   (d) securing the membrane using T-flat bars adhered to the horizontal bars;
   (e) adjusting the membrane stress using a handle placed on the side of one of the horizontal bars;
   (f) positioning the foot on the membrane and taking the image; and
   (g) double-sided machining the insole on the basis of the image of the surface provided in STL format.

2. The method for obtaining a plantar image using means for securing and tightening an elastic membrane, as well as double-sided machining the insole thus obtained, according to claim 1, wherein the membrane stress is capable of changing by removing the foot from the device.

3. A device for obtaining a plantar image using means for securing and tightening an elastic membrane, the device comprising:
   a structure formed by a plurality of support bars on which two horizontal bars passing through a scanner from one side to another are placed, these horizontal bars being adjustable both in height and distance there between due to the possibility of extending the support bars, wherein an elastic membrane is placed on the horizontal bars, adjusted using T-flat bars arranged in the horizontal bars, and which is tightened by means of a handle (5) rotating one of the horizontal bars according to the needs.

4. The device for obtaining a plantar image using means for securing and tightening an elastic membrane, according to claim 3 wherein the elastic membrane used in the scanner is made of natural rubber, silicone, or latex.

5. The device for obtaining a plantar image using means for securing and tightening an elastic membrane, according to claim 3 wherein the scanner is replaced by a plurality of cameras and a anti-reflective crystal, being crossed from one side to another by the horizontal bars.

6. The device for obtaining a plantar image using means for securing and tightening an elastic membrane, as well as the insole thus obtained, according to claim 5, wherein the horizontal bar capable of rotating has a ratchet mechanism at one of its ends for preventing unwanted rotation.

7. The device for obtaining a plantar image using means for securing and tightening the elastic membrane, according to claim 5, wherein the elastic membrane is used when the system has a plurality of cameras and the crystal, and the membrane is made of natural rubber, silicone, or latex.

8. The device for obtaining a plantar image using means for securing and tightening the elastic membrane according to claim 7, wherein the configuration of the bottom of the membrane has lines which may further have one or more lines with different thickness.

9. The device for obtaining a plantar image using means for securing and tightening the elastic membrane according to claim 8, wherein the geometric elements arranged at the bottom of the membrane displayed through the cameras are lines in a calculated orientation for minimizing to the maximum the multiple intersections with the epipolar ones.

10. The device for obtaining a plantar image using means for securing and tightening the elastic membrane according to claim 9, wherein the membrane has at least one line with a different thickness than the rest of the lines.

11. The device for obtaining a plantar image using means for securing and tightening an elastic membrane, according to claim 3, wherein the at least one horizontal bars is capable of rotating.

12. The method for obtaining a plantar image using a device with means for securing and tightening an elastic membrane, as well as double-sided machining the insole thus obtained, according to claim 1, wherein the machining step (g) of said method comprises the following operative stages:
   obtaining the insole contour;
   obtaining the machining paths;
   projecting the path points on the surface;
   calculating the end path; and
   cutting the insole, following the contour by using the tool, wherein the tool center is kept at a distance away from said contour equal to the radius thereof.

13. The method for obtaining a plantar image using a device with means for securing and tightening an elastic membrane, as well as machining the insole thus obtained, according to claim 12, wherein before the path calculation and after cutting the insole, breathing holes are made in a certain area of the insole.

14. The method for obtaining a plantar image using a device with means for securing and tightening an elastic membrane, as well as machining the insole thus obtained, according to claim 12, wherein the insole machining step (g) is automatically carried out by using a system for securing and rotating prismatic pieces, enabling said pieces to be rotated up to 180°.

* * * * *